US009301684B2

(12) United States Patent
Hara

(10) Patent No.: US 9,301,684 B2
(45) Date of Patent: Apr. 5, 2016

(54) OPHTHALMIC IMAGING APPARATUS, CONTROL METHOD FOR OPHTALMIC IMAGING APPARATUS, AND STORAGE MEDIUM

(71) Applicant: CANON KABUSHIKI KAISHA, Tokyo (JP)

(72) Inventor: Hiroshi Hara, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 351 days.

(21) Appl. No.: 14/066,909

(22) Filed: Oct. 30, 2013

(65) Prior Publication Data

US 2014/0132926 A1 May 15, 2014

(30) Foreign Application Priority Data

Nov. 9, 2012 (JP) ................................ 2012-247754

(51) Int. Cl.
*A61B 3/14* (2006.01)
*A61B 3/15* (2006.01)
*A61B 3/12* (2006.01)

(52) U.S. Cl.
CPC . *A61B 3/152* (2013.01); *A61B 3/12* (2013.01); *A61B 3/14* (2013.01)

(58) Field of Classification Search
CPC ............ A61B 3/12; A61B 3/14; A61B 3/145; A61B 3/152
USPC ................................................ 351/208, 246
See application file for complete search history.

(56) References Cited

U.S. PATENT DOCUMENTS

| 5,694,197 | A | 12/1997 | Tsukada et al. | |
|---|---|---|---|---|
| 8,585,203 | B2 * | 11/2013 | Aikawa et al. | A61B 3/152 351/205 |
| 8,757,801 | B2 | 6/2014 | Nakahara et al. | |
| 2006/0285075 | A1 | 12/2006 | Matsumura | |
| 2007/0013867 | A1 | 1/2007 | Ichikawa | |
| 2009/0323023 | A1 * | 12/2009 | Kogawa et al. | A61B 3/0033 351/208 |
| 2010/0182567 | A1 * | 7/2010 | Nouchi et al. | A61B 3/0041 351/208 |
| 2010/0253910 | A1 | 10/2010 | Mizuochi | |

(Continued)

FOREIGN PATENT DOCUMENTS

CN 102379683 A 3/2012
CN 102458228 A 5/2012

(Continued)

OTHER PUBLICATIONS

Apr. 3, 2015 Chinese Official Action in Chinese Patent Appln. No. 201310551729.3.

*Primary Examiner* — Huy K Mai
(74) *Attorney, Agent, or Firm* — Fitzpatrick, Cella, Harper & Scinto

(57) ABSTRACT

An ophthalmic imaging apparatus having an automatic transition function for transiting from an anterior ocular observation state to a fundus observation state, an autofocus function performed during fundus observation, and an automatic image capturing function performed when fundus alignment is complete, the apparatus comprising: a first control unit configured to control the automatic transition function, the autofocus function, and the automatic image capturing function to be deactivated in response to a first user operation; and a second control unit configured to control the deactivated automatic transition function, autofocus function, and automatic image capturing function to be reactivated in response to a second user operation.

7 Claims, 14 Drawing Sheets

(56) References Cited

U.S. PATENT DOCUMENTS

| | | |
|---|---|---|
| 2011/0170063 A1 | 7/2011 | Ooban et al. |
| 2012/0050515 A1 | 3/2012 | Shikaumi et al. |
| 2012/0050670 A1 | 3/2012 | Nakahara et al. |
| 2012/0050678 A1 | 3/2012 | Aoki |
| 2014/0226129 A1 | 8/2014 | Nakahara et al. |

FOREIGN PATENT DOCUMENTS

| | | |
|---|---|---|
| JP | 05-095902 A | 4/1993 |
| JP | 08-289874 A | 11/1996 |
| JP | 3490796 B2 | 1/2004 |
| JP | 2005-160549 A | 6/2005 |
| JP | 2009-172157 A | 8/2009 |

* cited by examiner

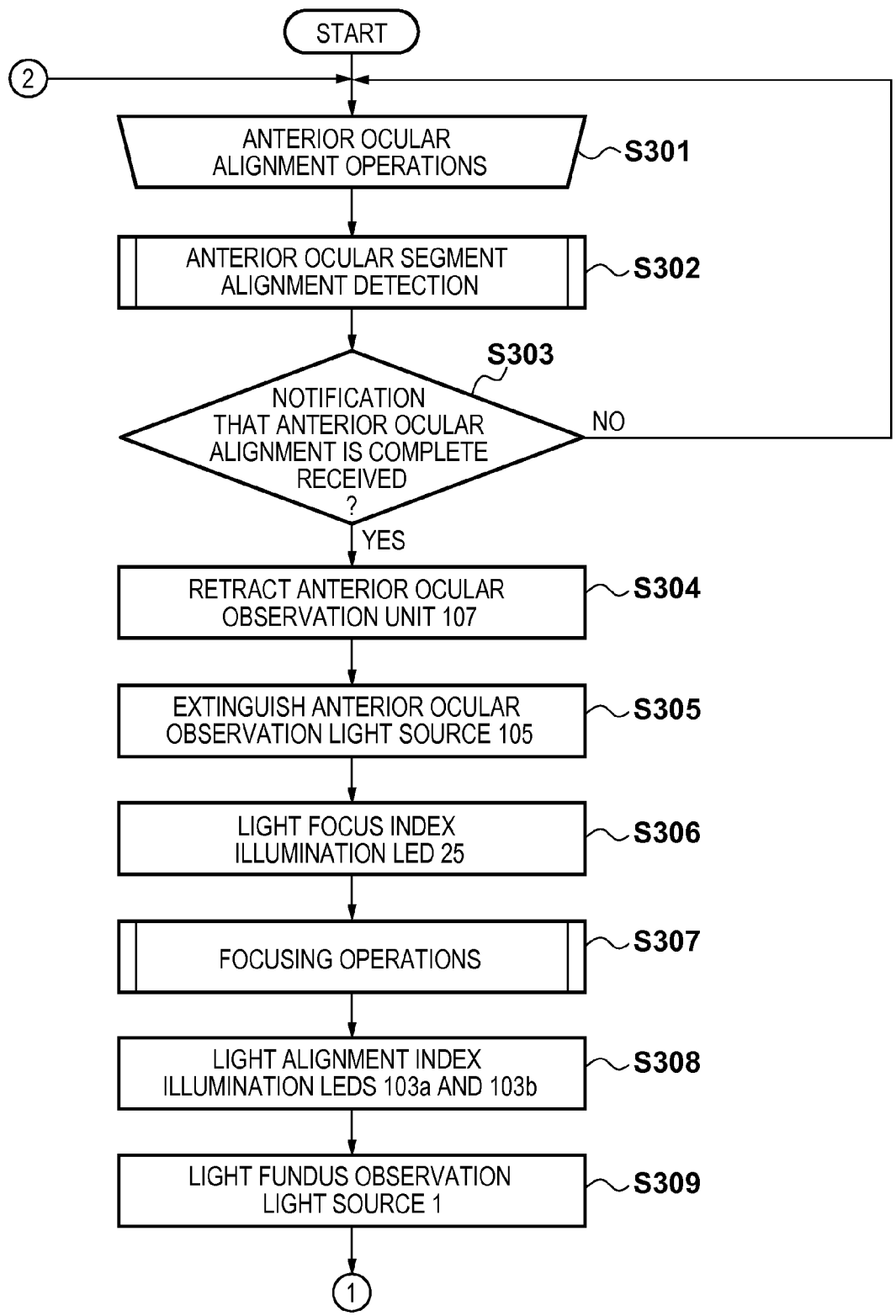

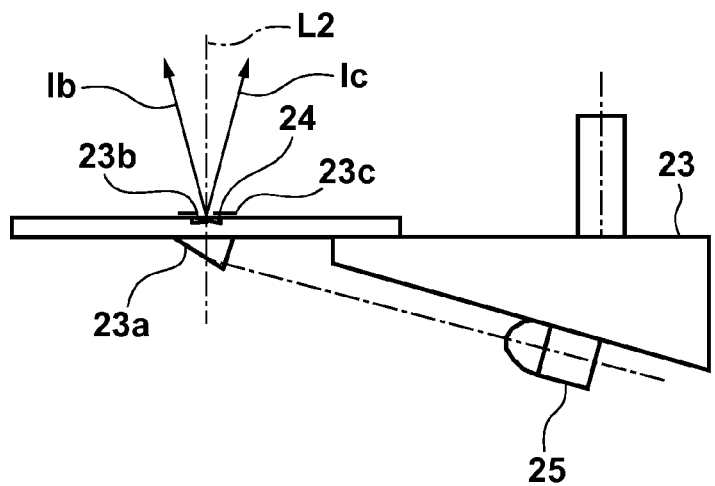
F I G. 12
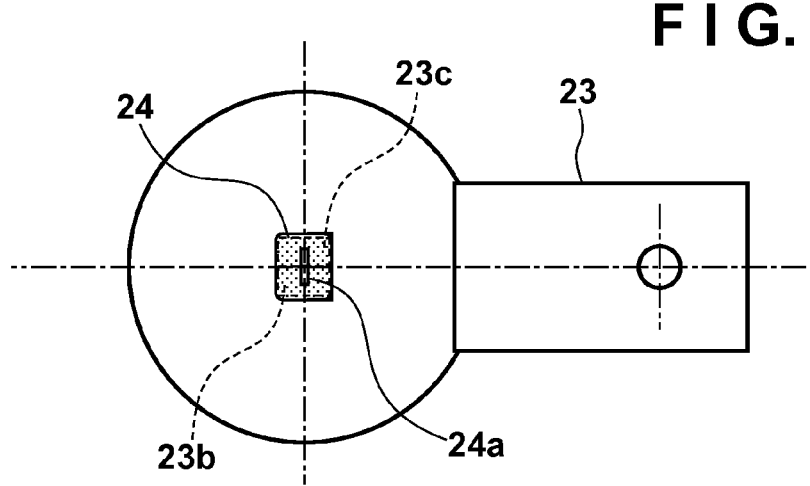
F I G. 13
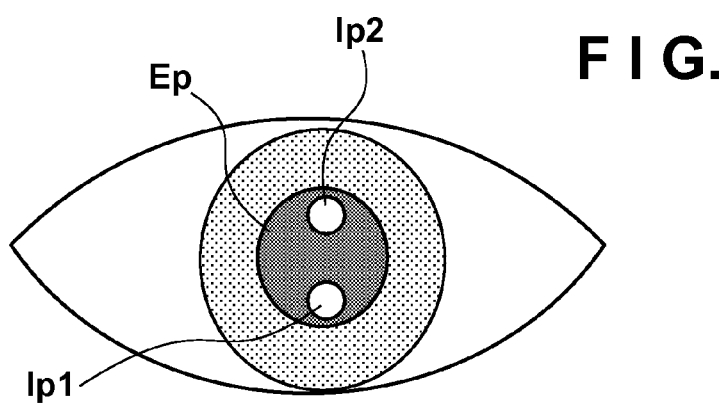
F I G. 14

OPHTHALMIC IMAGING APPARATUS, CONTROL METHOD FOR OPHTALMIC IMAGING APPARATUS, AND STORAGE MEDIUM

BACKGROUND OF THE INVENTION

1. Field of the Invention

The present invention relates to ophthalmic imaging apparatuses for observing or capturing images of the fundus of an eye to be examined, such as fundus cameras used in ophthalmological clinics, group health examinations, and the like, and further relates to control methods for such ophthalmic imaging apparatuses and storage medium.

2. Description of the Related Art

Fundus cameras that automatically execute alignment operations for aligning a fundus camera optical system with an eye to be examined and focus adjustment operations, in order to simplify those operations, have been proposed in the past (see Japanese Patent No. 3490796 and Japanese Patent Laid-Open No. 2005-160549).

Meanwhile, an ophthalmic imaging apparatus that has an autofocus function, an auto small pupil switching function, and an auto shoot function and that is capable of activating and deactivating these automatic functions individually has also been proposed (see Japanese Patent Laid-Open No. 2009-172157).

The fundus cameras disclosed in Japanese Patent No. 3490796 and Japanese Patent Laid-Open No. 2005-160549 are configured so that imaging processes are started when an imaging button is turned on, and then alignment adjustment, focus adjustment, and imaging are executed automatically, after which the processes end.

However, when capturing an image of a fundus, there are cases where an examiner changes the alignment state and the focus state based on the state of the eye to be examined after the alignment and focus have been automatically adjusted, and thus the fundus cameras disclosed in Japanese Patent No. 3490796 and Japanese Patent Laid-Open No. 2005-160549 have a problem in that these items cannot be changed because the imaging is carried out automatically.

As opposed to this, the ophthalmic imaging apparatus disclosed in Japanese Patent Laid-Open No. 2009-172157 is configured so that the autofocus function and auto shoot function can be activated and deactivated individually, and thus it is possible for the examiner to adjust the alignment and the focus.

However, it is necessary to activate or deactivate the respective functions before imaging operations are started, and thus there is a problem in that once imaging operations have been commenced with the autofocus function and the auto shoot function active, those functions cannot be dynamically deactivated after judging the state of the eye to be examined from an observation image of that eye, whose image is to be captured.

The ophthalmic imaging apparatus disclosed in Japanese Patent Laid-Open No. 2009-172157 is configured having preset conditions that deactivate the autofocus function and the auto shoot function operations, where the autofocus function and the auto shoot function are deactivated when those conditions are met; however, this configuration requires the conditions for deactivating the operations to be set in advance, and there is thus a problem in that the functions cannot be dynamically deactivated during imaging operations.

Meanwhile, when capturing an image of an eye to be examined that has opacity in the crystalline lens, such as with cataracts, the fundus of the eye to be examined is observed, a region in the fundus observation image free of cloudiness is searched out, and the focusing is completed through that region. With this type of operation, there is demand for the ability to manually change the focus region, but then execute an autofocus function in the region where focusing can be carried out.

However, Japanese Patent No. 3490796, Japanese Patent Laid-Open No. 2005-160549, and Japanese Patent Laid-Open No. 2009-172157 have problems in that the autofocus function and the auto shoot function cannot be changed from inactive to active during imaging operations.

Accordingly, with conventional ophthalmic imaging apparatuses, it is difficult to carry out operations that meet an examiner's needs.

SUMMARY OF THE INVENTION

The present invention provides a technique for improving the operability of an ophthalmic imaging apparatus for an examiner.

According to one aspect of the present invention, there is provided an ophthalmic imaging apparatus having an automatic transition function for transiting from an anterior ocular observation state to a fundus observation state, an autofocus function performed during fundus observation, and an automatic image capturing function performed when fundus alignment is complete, the apparatus comprising: a first control unit configured to control the automatic transition function, the autofocus function, and the automatic image capturing function to be deactivated in response to a first user operation; and a second control unit configured to control the deactivated automatic transition function, autofocus function, and automatic image capturing function to be reactivated in response to a second user operation.

Further features of the present invention will become apparent from the following description of exemplary embodiments (with reference to the attached drawings).

BRIEF DESCRIPTION OF THE DRAWINGS

FIGS. 3A and 3B are flowcharts illustrating operations performed by the ophthalmic imaging apparatus according to the first embodiment.

FIG. 12 is a diagram illustrating a focus index projection unit according to the first embodiment.

FIG. 13 is a diagram of the focus index projection unit according to the first embodiment observed from the direction of an optical axis L2.

FIG. 14 is a diagram illustrating positions of focus index light fluxes on the pupil of an eye to be examined according to the first embodiment.

DESCRIPTION OF THE EMBODIMENTS

Figure 1A:
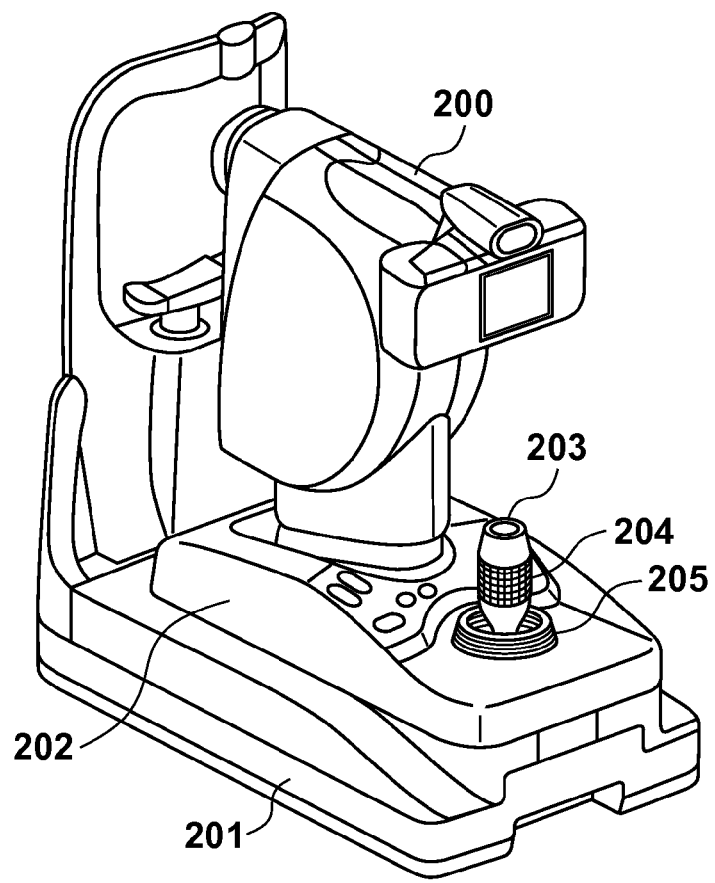
FIGS. 1A and 1B are diagrams illustrating the overall configuration of an ophthalmic imaging apparatus according to a first embodiment.

Exemplary embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

Furthermore, throughout the embodiments of the present invention, identical reference numerals indicate identical constituent elements.

First Embodiment

Figure 1B:
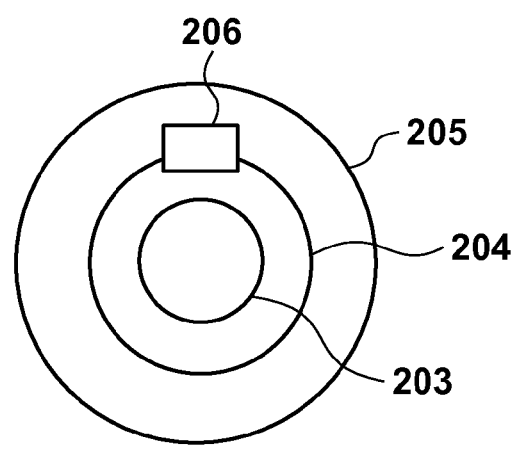

FIG. 1A is a diagram illustrating an overview of a fundus camera serving as an ophthalmic imaging apparatus embodying the present invention, whereas FIG. 1B is a schematic diagram illustrating the configuration of a focus manipulation portion and a joystick portion illustrated in FIG. 1A.

An optical main body 200 that includes an optical system for observing/imaging an eye to be examined is anchored to a movable stage 202 capable of moving forward/backward and left/right upon a fixed base 201. A joystick 204 including a focus manipulation unit 205, an imaging switch 203, and an alignment toggle switch 206 is provided on the movable stage 202. By operating the joystick 204, an examiner can move the movable stage 202 to a desired position, and by manipulating the focus manipulation unit 205, the examiner can adjust the focal position on an eye to be imaged.

The imaging switch 203 is configured so as to be depressible in two stages. The functions implemented when the imaging switch 203 is depressed to the first stage and depressed to the second stage, respectively, will be described later.

Figure 2:
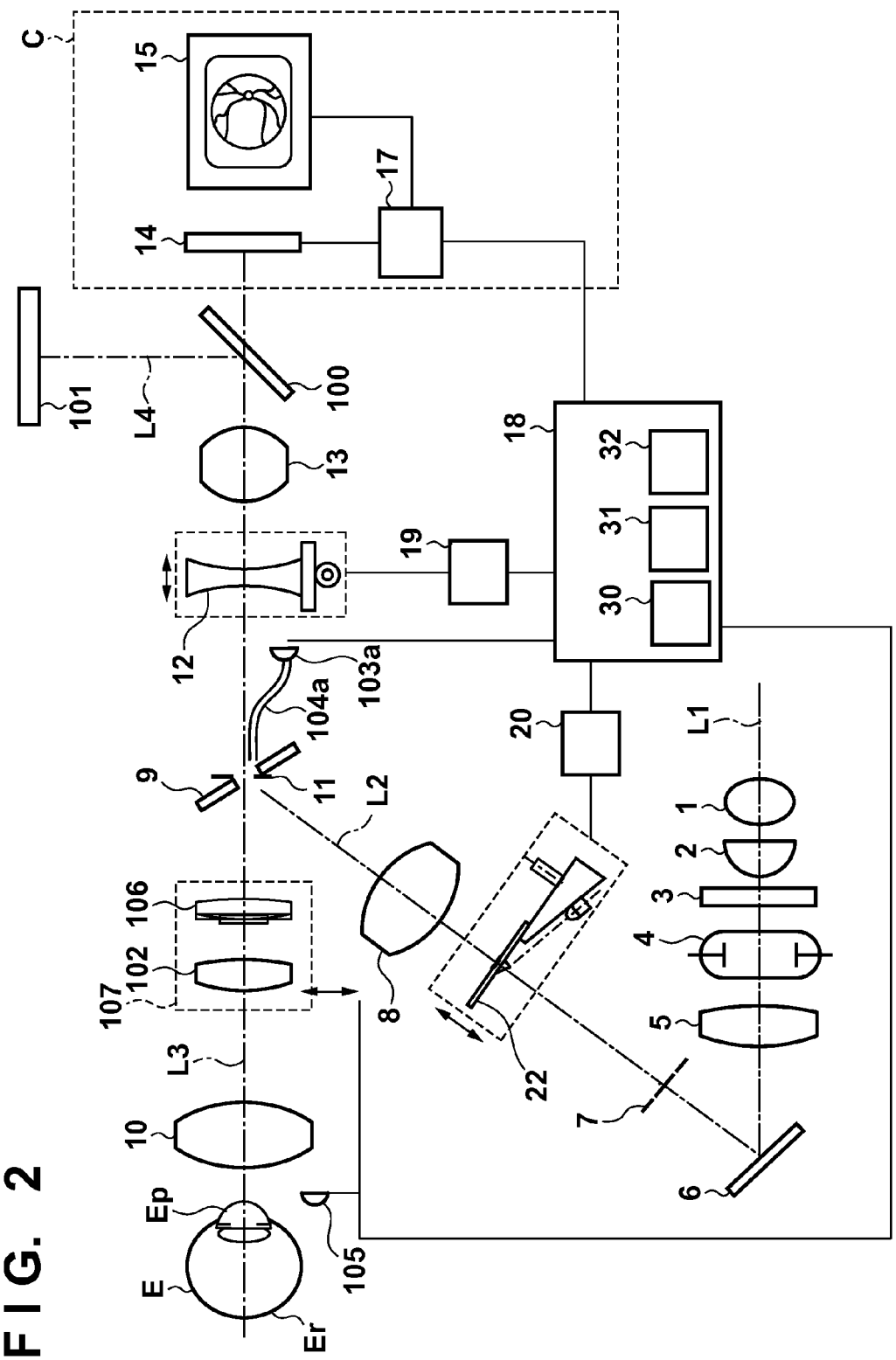
FIG. 2 is a diagram illustrating an exemplary configuration of the ophthalmic imaging apparatus according to the first embodiment.

FIG. 2 is a diagram illustrating an exemplary configuration of an ophthalmic imaging apparatus according to the present embodiment. An observation light source 1 that emits stationary light such as a halogen lamp, a condenser lens 2, a filter 3 that transmits infrared light but blocks visible light, an imaging light source 4 such as a strobe, a lens 5, and a mirror 6 are disposed in an optical axis L1; a ring aperture 7 having a ring-shaped aperture, a relay lens 8, and a perforated mirror 9 having an aperture in the center thereof are disposed in that order in the optical axis L2 that follows the direction of light reflected by the mirror 6.

Furthermore, an anterior ocular observation unit 107 including an auxiliary lens 102 for observing an anterior ocular segment and a prism lens 106 having an image splitting prism that divides a light flux into positions conjugate with the anterior ocular segment of an eye to be examined E, and an objective lens 10 that opposes the eye to be examined E, are disposed in an optical axis L3 that follows the direction of light reflected by the perforated mirror 9; the anterior ocular observation unit 107 is capable of entering into/retracting from the optical axis L3. An imaging aperture 11 provided in the opening of the perforated mirror 9, a focusing lens 12 that adjusts the focus by moving along the optical axis L3, an imaging lens 13, and a half mirror 100 are disposed in that order along the optical axis L3. The image sensor 14, which can be used for real-time observation as well as capturing still images, is provided after the half mirror 100 within an imaging camera C, and an internal fixation light 101 is disposed at the end of an optical axis L4 that follows the direction of the light reflected by the half mirror 100. The image sensor 14 can be made sensitive to both visible light wavelengths and infrared light wavelengths, and can thus be configured to be capable of capturing infrared images as well. Meanwhile, an output end of a light guide 104a that guides a light flux from an LED light source 103a is disposed at the front surface of the perforated mirror 9, and this output end serves as an alignment index P1. The alignment index P1 is disposed outside of the optical axis L3, and the output end of a light guide 104b (not shown) that guides a light flux from an LED light source 103b (not shown) emitting light of the same wavelength as the LED light source 103a is disposed so as to be symmetrically positioned relative to the alignment index P1 around the optical axis L3; this output end serves as an alignment index P2, and the alignment index P1 and alignment index P2 configure an alignment index projection optical system.

Here, an output of the image sensor 14 is sent to an image processing unit 17, and an output of the image processing unit 17 is sent to a system control unit 18. The image processing unit 17 projects the observation image formed by the image sensor 14 in the monitor 15.

On the other hand, a focus index projection unit 22 is disposed in the optical axis L2 between the ring aperture 7 and the relay lens 8. Details of the focus index projection unit 22 will be given later. Note that the focus index projection unit 22 and the focusing lens 12 are moved in tandem along the optical axis L2 and the optical axis L3 by a focus lens driving unit 19 and a focus index driving unit 20, respectively, under control performed by the system control unit 18. The system control unit 18 detects whether the examiner has manipulated the focus manipulation unit 205 and carries out control for switching between a manual focus mode and automatic focus mode; in the manual focus mode, the system control unit 18 controls the focus lens driving unit 19 and the focus index driving unit 20 in accordance with the operations made through the focus manipulation unit 205. At this time, the focus index projection unit 22 and the image sensor 14 are in an optically conjugate relationship. Meanwhile, in the automatic focus mode, the system control unit 18 controls the focus lens driving unit 19 and the focus index driving unit 20 based on the result of a detection performed by a focusing operation unit 30. The system control unit 18 also includes an anterior ocular segment alignment detection unit 31. During an automatic alignment switching mode, the system control unit 18 determines that alignment is complete based on a detection result from the anterior ocular segment alignment detection unit 31, and in the case where the anterior ocular observation unit 107 is inserted into the optical axis L3, the system control unit 18 retracts the anterior ocular observation unit 107 from the optical axis L3 and changes an area of observation from the anterior ocular segment to the fundus. On the other hand, during a manual alignment switching mode, the anterior ocular observation unit 107 is inserted and retracted based on manipulation of the alignment toggle switch 206. The system control unit 18 also includes a fundus segment alignment detection unit 32. During an automatic imaging mode, the system control unit 18 determines that alignment is complete based on a detection result from the fundus segment alignment detection unit 32, and in the case where the anterior ocular observation unit 107 is retracted from the optical axis L3, the system control unit 18 carries out an image capturing process by manipulating the imaging switch 203. On the other hand, during a manual imaging mode, the image capturing process is carried out based on the examiner manipulating the imaging switch 203.

The system control unit 18 also performs control for adjusting a light amount of, lighting, and extinguishing the observation light source 1, as well as control for adjusting a light amount of, lighting, and extinguishing the imaging light source 4.

Next, operations performed by the system control unit 18 according to the present embodiment will be described. First, with the observation light source 1 extinguished, the system control unit 18 lights an anterior ocular segment observation light source 105. A light flux emitted from the anterior ocular segment observation light source 105 is reflected and scattered by the anterior ocular segment of the eye to be examined E, and forms an image on the image sensor 14 after passing through the objective lens 10, the anterior ocular observation unit 107, the imaging aperture 11, the focusing lens 12, the imaging lens 13, and the half mirror 100. The image processing unit 17 then projects the anterior ocular segment image formed on the image sensor 14 in the monitor 15.

The examiner moves the movable stage 202 by manipulating the joystick 204 while observing the anterior ocular segment image projected in the monitor 15, and roughly adjusts the positioning between the eye to be examined E and the optical unit. The examiner then depresses the alignment toggle switch 206 and observes the fundus segment.

Next, the system control unit 18 retracts the anterior ocular observation unit 107 from the optical axis L3, extinguishes the anterior ocular segment observation light source 105, and lights the observation light source 1. A light flux emitted from the observation light source 1 is condensed by the condenser lens 2, after which the filter 3 cuts the visible light therefrom and transmits only the infrared light; the infrared light then traverses the imaging light source 4 such as a strobe, is converted to a ring-shaped light flux by the lens 5, the mirror 6, and the ring aperture 7, is deflected in the direction of the optical axis L3 by the relay lens 8 and the perforated mirror 9, traverses a pupil Ep via the objective lens 10, and illuminates a fundus Er of the eye to be examined E. The light flux that has reached the fundus Er is reflected and scattered, emitted from the eye to be examined E, and forms an image on the image sensor 14 after traversing the objective lens 10, the imaging aperture 11, the focusing lens 12, the imaging lens 13, and the half mirror 100. The image processing unit 17 then projects the fundus image formed on the image sensor 14 in the monitor 15.

The examiner then finely adjusts the positioning between the eye to be examined E and the optical unit while observing the fundus image projected in the monitor 15, adjusts the focus, and depresses the imaging switch 203 to capture an image. The present embodiment describes an ophthalmic imaging apparatus that includes not only the aforementioned automatic alignment switching function that automatically changes the area of observation from the anterior ocular segment to the fundus segment and an autofocus function that automatically adjusts the focus, but also an automatic image capturing function that automatically captures an image.

In order to execute the automatic alignment switching function, the output of the image processing unit 17 is sent to the system control unit 18, and is sent to the anterior ocular segment alignment detection unit 31 provided in the system control unit 18. Furthermore, the anterior ocular segment alignment detection unit 31 is connected to a driving unit (not shown) that drives the anterior ocular observation unit 107, and an automatic alignment switching operation is carried out by that driving unit.

In order to execute the autofocus function, the output of the image processing unit 17 is sent to the system control unit 18, and is sent to the focusing operation unit 30 provided in the system control unit 18. Furthermore, the focus operation unit 30 is connected to the focus lens driving unit 19 and the focus index driving unit 20, and an autofocus operation is carried out by control performed by these driving units.

In order to execute the automatic image capturing function, the output of the image processing unit 17 is sent to the system control unit 18, and is sent to the fundus segment alignment detection unit 32 provided in the system control unit 18. Furthermore, the fundus segment alignment detection unit 32 is connected to the imaging switch 203, and an automatic imaging operation is carried out using this configuration.

Functions of the focus index projection unit 22 will now be described. As shown in FIG. 12, a light flux from a focus index illumination LED 25 is deflected in the direction of the optical axis L2 by a prism portion 23*a* of a focusing split prism 23 and reaches prism portions 23*b* and 23*c*. Here, the prism portions 23*b* and 23*c* have prism surfaces having angles that are symmetrical to each other. The light flux that has reached the prism portions 23*b* and 23*c* passes through a rectangular aperture portion 24*a* of a focus index 24 shown in FIG. 13, resulting in two focus index light fluxes lb and lc that are symmetrical relative to the optical axis L2; the focus index light fluxes lb and lc then reach the eye to be examined E via the relay lens 8, the perforated mirror 9, and the objective lens 10.

Figure 11:
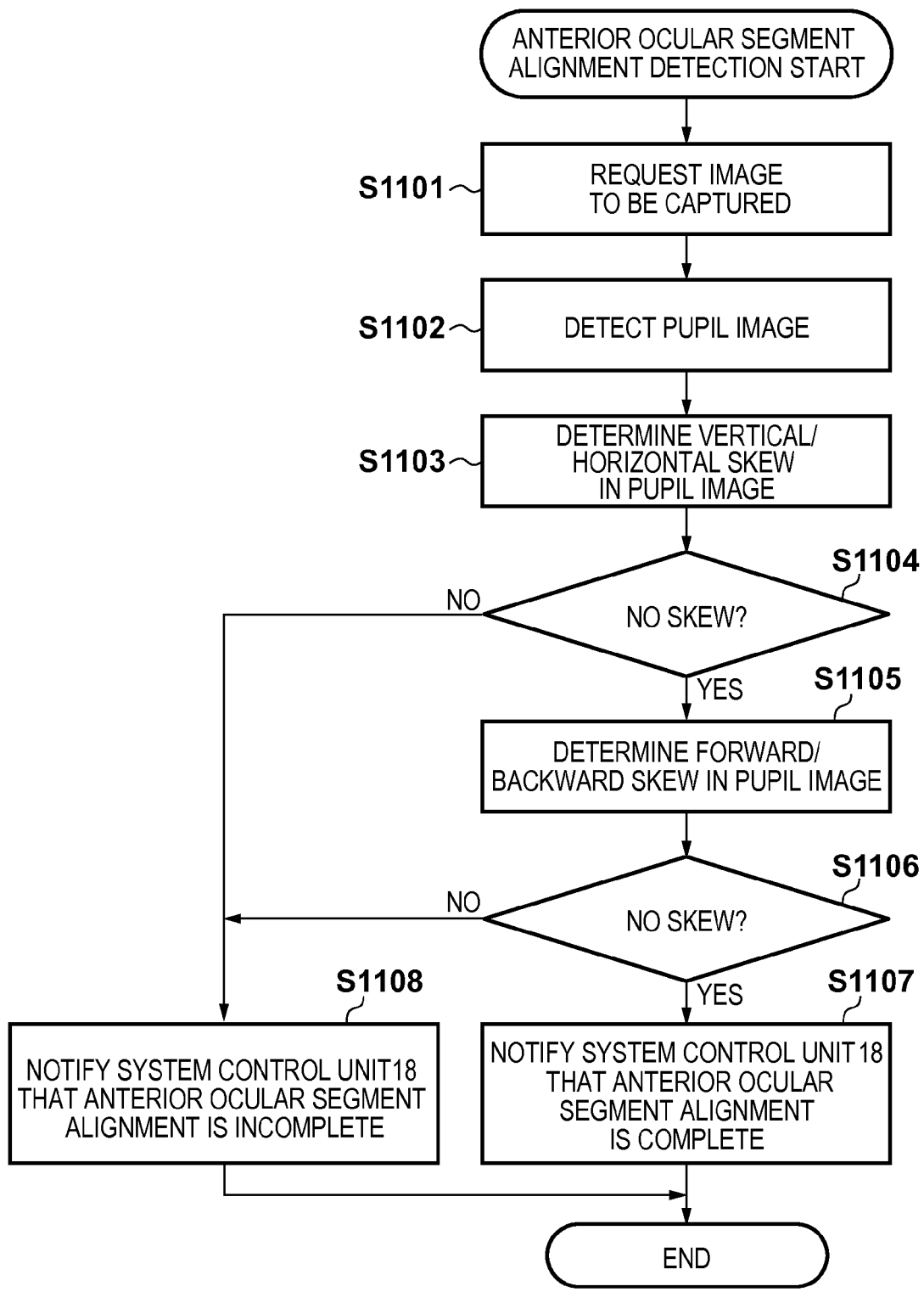
FIG. 11 is a flowchart illustrating operations performed by an anterior ocular segment alignment detection unit according to the first embodiment.
Figure 15:
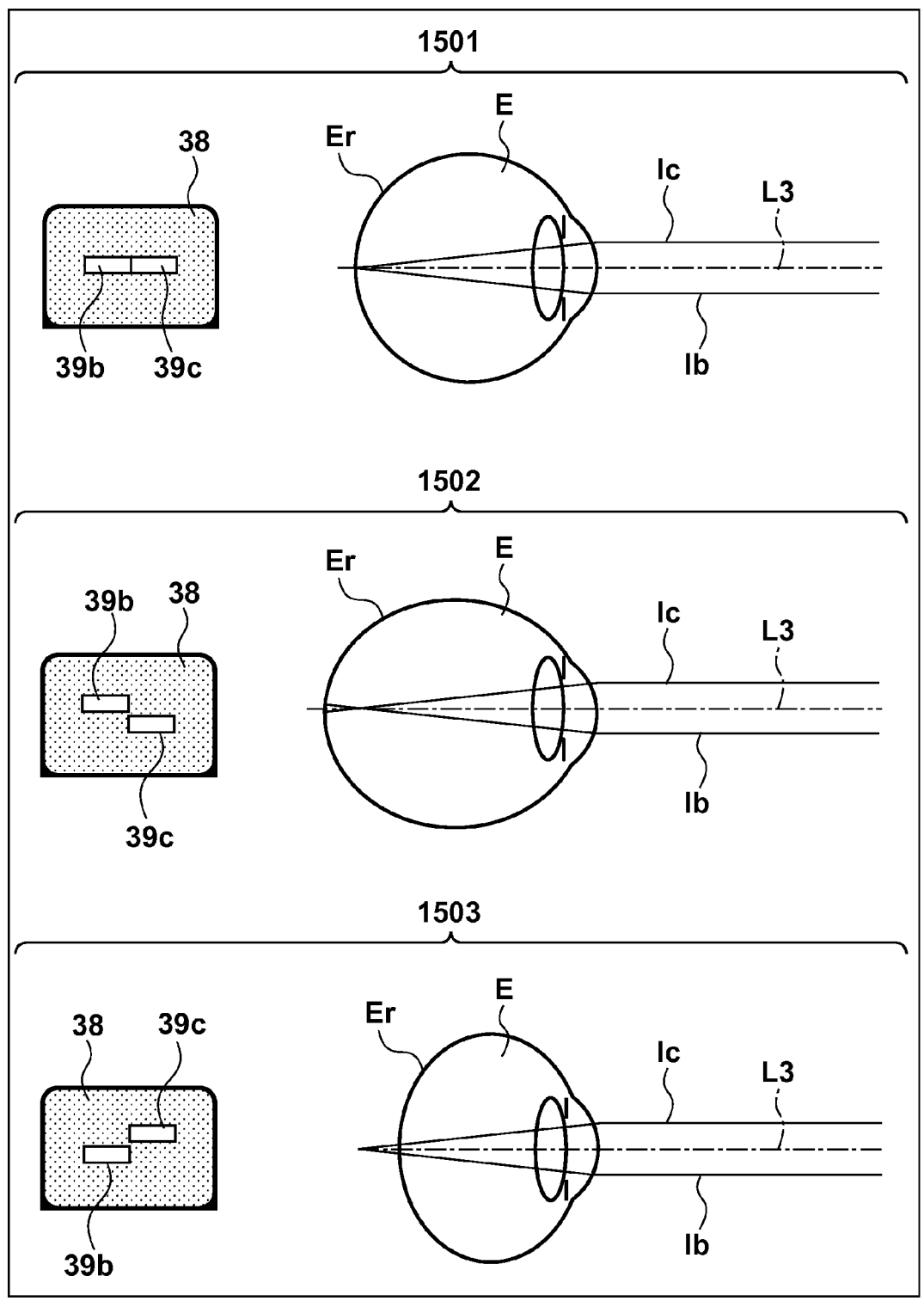
FIG. 15 is a diagram illustrating focus index functions according to the first embodiment.

FIG. 11 lp1 of the focus index light flux lb on the pupil Ep of the eye to be examined E and a position 1p2 of the focus index light flux 1c on the pupil Ep of the eye to be examined E.

In FIGS. 15, 1501, 1502, and 1503 respectively indicate the focus index light fluxes lb and lc reaching the fundus Er of the eye to be examined E, and focus index images 39*b* and 39*c* produced by the focus index light fluxes 1*b* and 1*c* on the fundus Er.

1501 is a diagram illustrating a case where the fundus Er of the eye to be examined E and the focus index 24 are in an optically conjugate positional relationship. Because the fundus Er and the focus index 24 are optically conjugate, the two focus index light fluxes lb and lc being split into two fluxes result, on the fundus Er, images 39*b* and 39*c* of the rectangular aperture portion 24*a* in the focus index 24 (these images will be referred to as the focus index images 39*b* and 39*c* hereinafter), and the images are arranged in a row.

1502 illustrates a case where the eye to be examined E is more nearsighted than in 1501. In this case, the fundus Er and the focus index 24 are not optically conjugate, and thus the focus index light fluxes 1*b* and 1*c* being split into two fluxes result, on the fundus Er, the focus index images 39*b* and 39*c* in a vertically-skewed state, with the focus index image 39*b* shifted upward and the focus index image 39*c* shifted downward.

1503 illustrates a case where the eye to be examined E is more farsighted than in 1501. In this case, the fundus Er and the focus index 24 are not optically conjugate, and thus the focus index light fluxes lb and lc being split into two fluxes result, on the fundus Er, the focus index images 39b and 39c in a vertically-skewed state, with the focus index image 39b shifted downward and the focus index image 39c shifted upward.

Autofocus methods in conventional fundus cameras detect the focus index images 39b and 39c and take measures to align the focus index images 39b and 39c in a row. In other words, the fundus Er and the focus index 24 are made optically conjugate. Then, because the focus index 24 and the image sensor 14 are in an optically conjugate relationship, the fundus Er and the image sensor 14 can enter an optically conjugate relationship as well by the focus lens driving unit 19 that drives the focusing lens 12 and the focus index driving unit 20 that drives the focus index 24 operating under a focus link; this makes it possible to bring the fundus Er into focus.

Next, operations performed by the anterior ocular segment alignment detection unit 31 for realizing the automatic alignment switching function according to the present embodiment will be described using FIGS. 9, 10, and 11.

Figure 9:
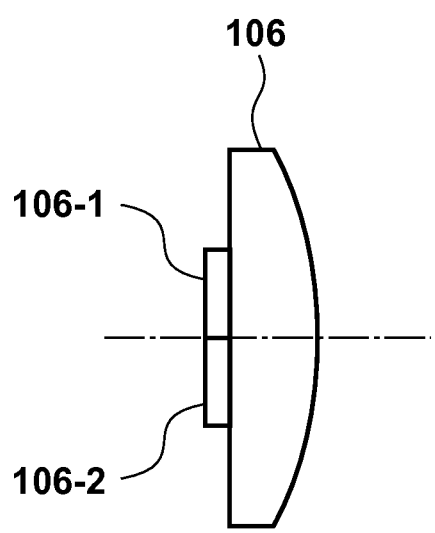
FIG. 9 is a diagram illustrating in detail a prism lens 106 according to the first embodiment.

FIG. 9 is a diagram illustrating in detail the prism lens 106 having the image splitting prism that divides the light flux into positions conjugate to the anterior ocular segment of the eye to be examined E, and of which the anterior ocular observation unit 107 is partially configured. Fresnel prisms 106-1 and 106-2 are provided in the prism lens 106 in positions that are conjugate to the anterior ocular segment of the eye to be examined E. The surface of the prism lens 106 on the opposite side as the Fresnel prisms 106-1 and 106-2 is convex, and serves as a field lens for the anterior ocular segment of the eye to be examined E.

Figure 10:
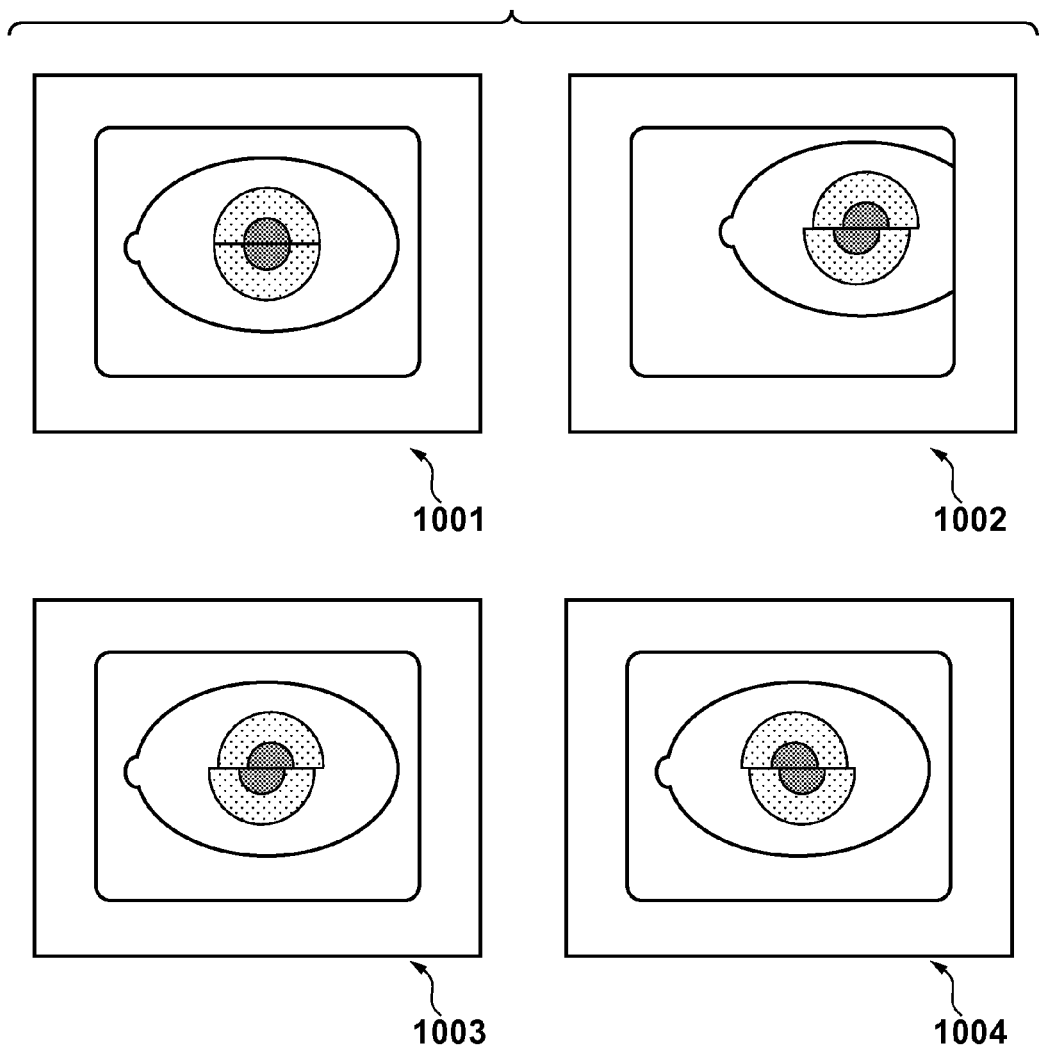
FIG. 10 is a diagram illustrating an example of an anterior ocular image captured by an image sensor 14 according to the first embodiment.

In the case where the positional relationship between the ophthalmic imaging apparatus and the eye to be examined E, or in other words, the alignment position, is an ideal position, the light flux from the anterior ocular segment of the eye to be examined E forms an image on the Fresnel prisms 106-1 and 106-2 of the prism lens 106, and the image is then split due to the prism effect; because the imaging surface of the image sensor 14 is also conjugate to the Fresnel prisms 106-1 and 106-2, an anterior ocular image such as that indicated by 1001 in FIG. 10 is formed on the image sensor 14. In the case where the alignment position is not in the ideal position in all of the X, Y, and Z directions, the anterior ocular image will be as indicated by 1002 in FIG. 10. However, in the case where the alignment position is in the ideal position in the X and Y directions but is too far in the Z direction, the anterior ocular image will be as indicated by 1003 in FIG. 10; in the case where the alignment position is too close in the Z direction, the anterior ocular image will be as indicated by 1004 in FIG. 10.

Next, operations performed by the anterior ocular segment alignment detection unit 31 will be described with reference to the flowchart in FIG. 11. When an anterior ocular segment alignment detection process is started, first, in S1101, the anterior ocular segment alignment detection unit 31 requests the image sensor 14 to capture an image. At this time, the light source for capturing the image is set to an infrared wavelength, thus preventing the pupil of the eye to be examined E from constricting.

In S1102, the anterior ocular segment alignment detection unit 31 detects a pupil image from the image captured in S1101. The pupil image is detected by, for example, focusing on the difference of brightness among the periphery of the pupil, the iris, and the pupil, and binarizing the captured image using a threshold that enables only the pupil image to be extracted from the image.

In S1103, the anterior ocular segment alignment detection unit 31 determines whether or not there is vertical and horizontal skew in the pupil image. Whether or not there is vertical and horizontal skew in the pupil image is determined by, for example, first finding a center position of the pupil image detected in S1102 and then finding a difference between the center position of the pupil image and a center position of the image sensor 14; it is determined that there is skew in the case where the difference between the center positions is greater than or equal to a threshold, whereas it is determined that there is no skew in the case where the difference between the center positions is less than the threshold.

In the case where the result of the determination performed in S1103 indicates that there is no skew, the procedure branches at S1104 and advances to S1105. On the other hand, in the case where the result of the determination performed in S1103 indicates that there is skew, the procedure advances to S1108.

In S1105, the anterior ocular segment alignment detection unit 31 determines whether or not there is forward/backward skew in the pupil image. Determining whether or not there is forward/backward skew in the pupil image is carried out by, for example, determining whether or not the shape of the pupil image detected in S1102 is divided by the Fresnel prisms 106-1 and 106-2. It can be determined that there is no skew in the case where the pupil image is circular in shape. In the case where the result of the determination performed in S1105 indicates that there is skew, the procedure branches at S1106 and advances to S1108. On the other hand, in the case where the result of the determination performed in S1105 indicates that there is no skew, the procedure branches at S1106 and advances to S1107.

In S1107, the anterior ocular segment alignment detection unit 31 notifies the system control unit 18 that the anterior ocular segment alignment is complete and ends the process. However, in the case where the process has advanced to S1108 from S1104 or S1106, in S1108, the anterior ocular segment alignment detection unit 31 notifies the system control unit 18 that the anterior ocular segment alignment is incomplete and ends the process.

Figure 4:
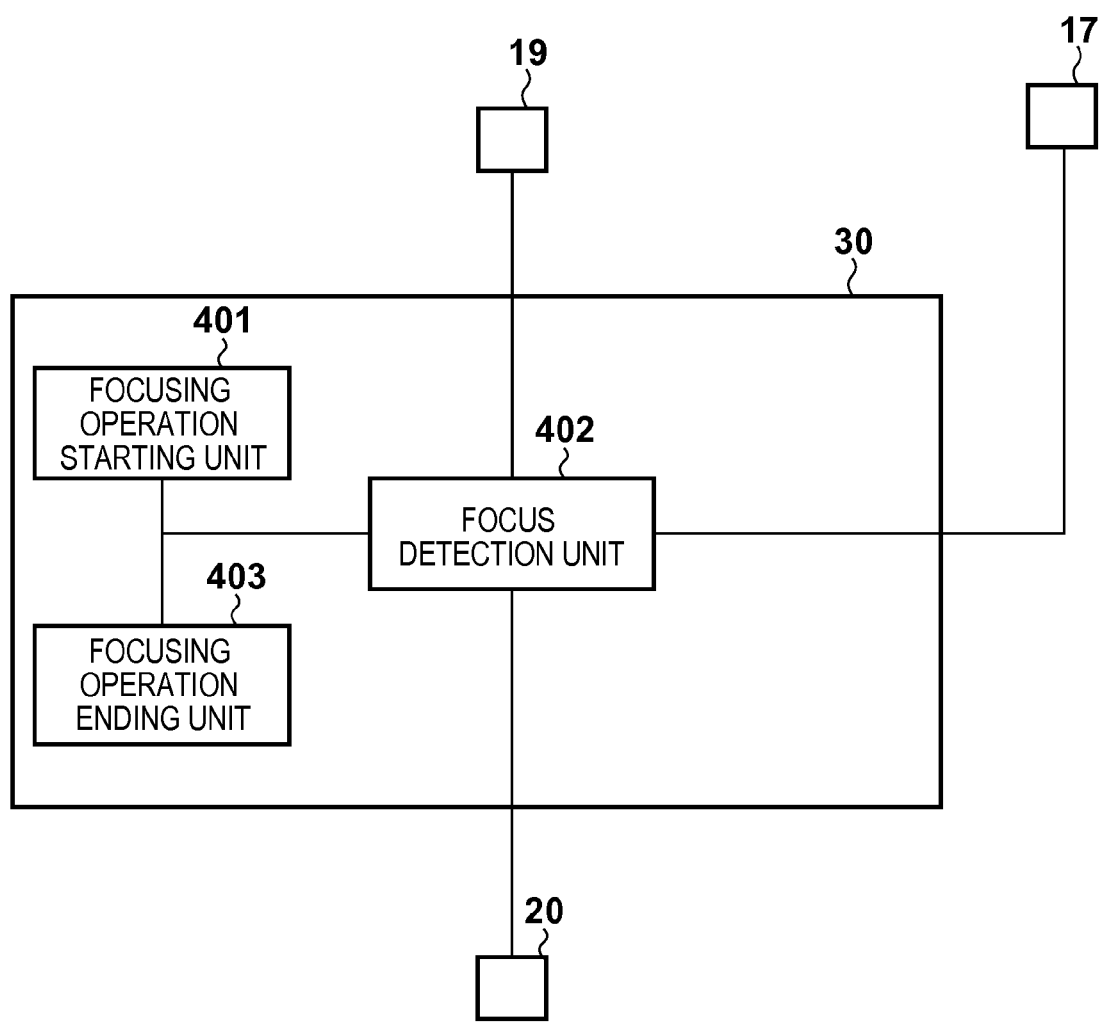
FIG. 4 is a diagram illustrating the configuration of a focusing operation unit according to the first embodiment.

Next, the focusing operation unit 30 for implementing the autofocus function according to the present embodiment will be described in detail with reference to FIG. 4. The focusing operation unit 30 includes a focusing operation starting unit 401, a focus detection unit 402, and a focusing operation ending unit 403 used for focusing. Of these, the focusing operation starting unit 401 and the focusing operation ending unit 403 are connected to the focus detection unit 402, and manage the execution of the focusing operations. Meanwhile, images sent from the image processing unit 17 are input into the focus detection unit 402, and can be output to the focus lens driving unit 19 and the focus index driving unit 20. Accordingly, the execution of focusing operations can be managed by the focus detection unit 402 that performs detection of a state of focus and output for the focusing operations, and by the focusing operation starting unit 401 and the focusing operation ending unit 403.

Figure 5:
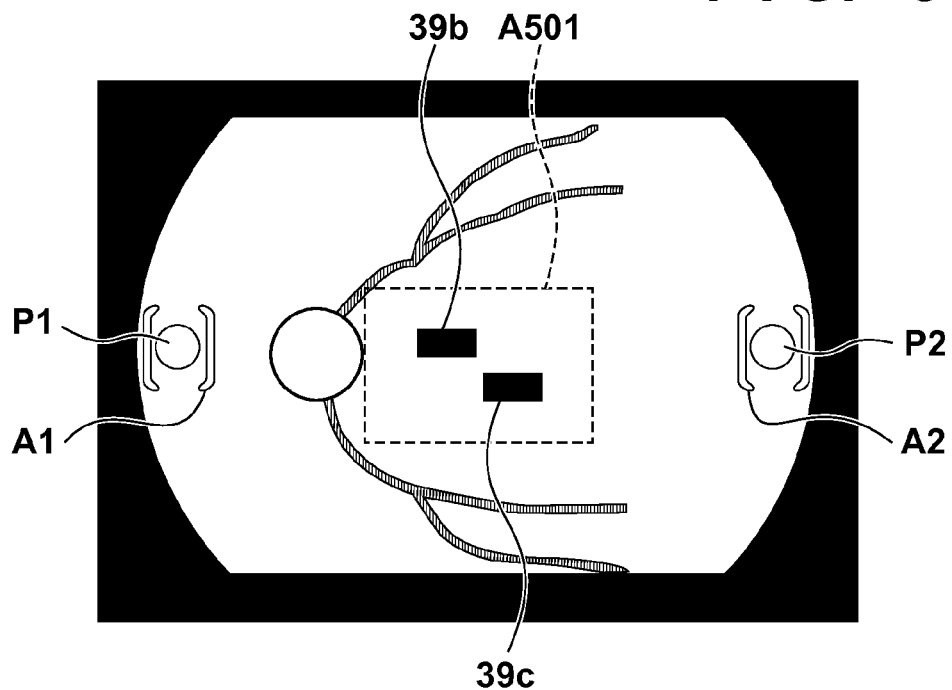
FIG. 5 is a diagram illustrating an example of a fundus image projected in a monitor 15 according to the first embodiment.

First, to describe the autofocus operation, a focus detection position detected by the focus detection unit 402 will be described using FIG. 5. FIG. 5 is a diagram illustrating the fundus image projected in the monitor 15, and a region A501 in FIG. 5 corresponds to the focus detection position for the focus detection unit 402. As illustrated here, the region A501 contains focus index images including the focus index image 39*b* and the focus index image 39*c*.

Note that P1 and P2 in FIG. 5 correspond to the alignment indexes P1 and P2 used for positioning the ophthalmic imaging apparatus and the eye to be examined as described with reference to FIGS. 1A and 1B, and guide frames A1 and A2 are displayed for the alignment indexes P1 and P2.

Next, operations performed by the focusing operation unit 30 will be described using FIG. 6 and the flowchart in FIG. 7.

In S701, the focusing operation starting unit 401 provided in the focusing operation unit 30 starts detecting a position of luminance in the focus index image projected onto the fundus. It is assumed that the focus index image at this time is as shown in FIG. 6.

Figure 6:
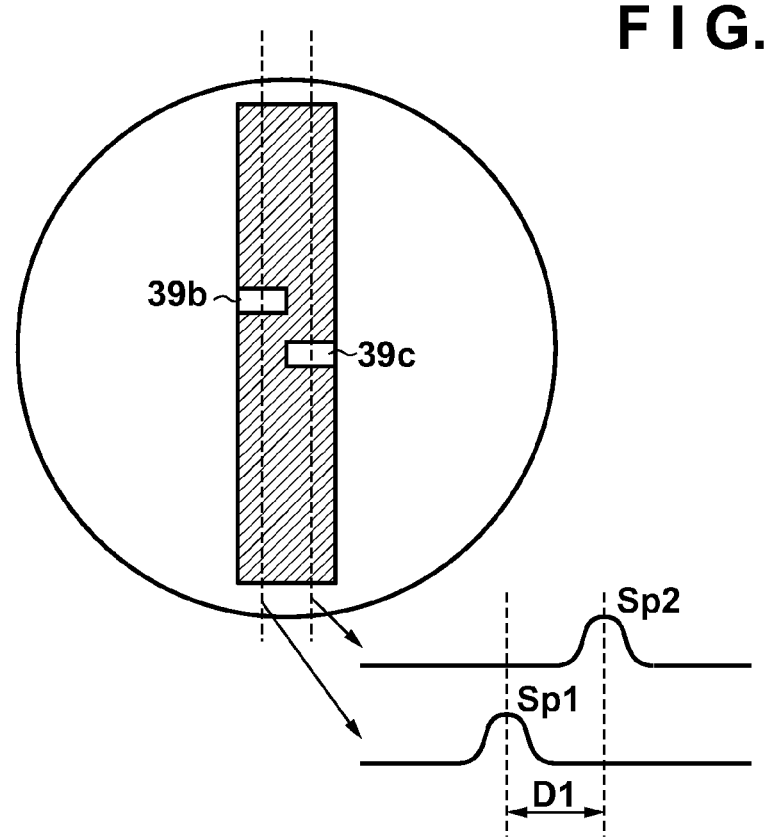
FIG. 6 is a diagram illustrating focal position detection performed by the focusing operation unit according to the first embodiment.
Figure 7:
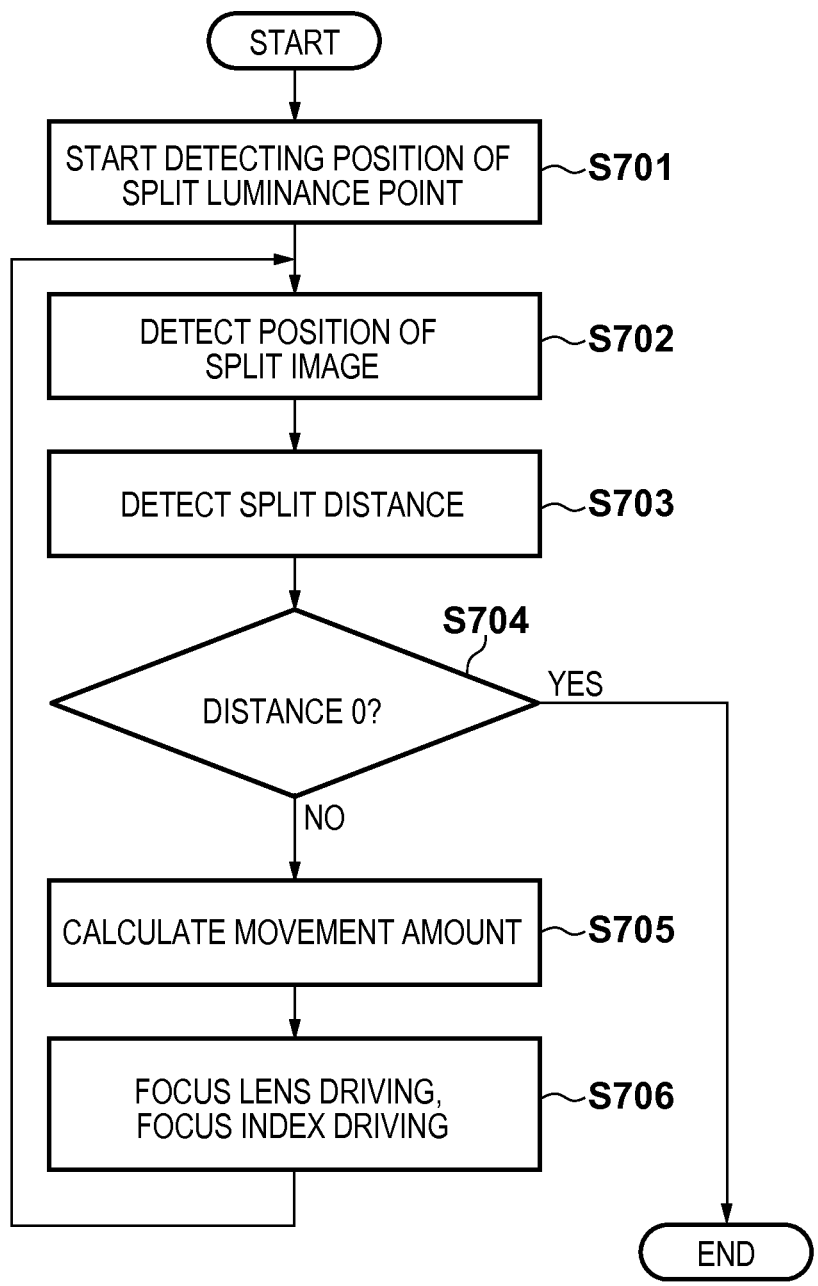
FIG. 7 is a flowchart illustrating operations performed by the focusing operation unit according to the first embodiment.

In S702, the focus detection unit 402 provided in the focusing operation unit 30 detects a region, indicated by hatching in FIG. 6, spanning from a left end of the focus index image 39*b* to a right end of the focus index image 39*c*.

Next, in S703, the focus detection unit 402 executes a scan in the vertical direction in FIG. 6, detecting a peak position SP1 and a peak position SP2 for the focus index image 39*b* and the focus index image 39*c*, respectively, that have been detected in S702; the focus detection unit 402 then calculates a distance D1 based on a positional relationship between the two peak positions.

The focusing operation unit 30 can calculate the distance D1 based on the positional relationship between the focus index image 39*b* and the focus index image 39*c*, and can detect the focal position, through the processes of S701 to S703 as described above.

Next, in S704, the focusing operation ending unit 403 provided in the focusing operation unit 30 ends the focusing operations performed by the focusing operation unit 30 in the case where the distance D1 calculated in S703 is 0. On the other hand, the focusing operations performed by the focusing operation unit 30 are continued in the case where the distance D1 calculated in S703 is not 0.

Next, in S705, the focus detection unit 402 calculates a focus movement amount corresponding to the distance D1 calculated in S703. In S706, the focus detection unit 402 performs focus lens driving and focus index driving using the focus lens driving unit 19 and the focus index driving unit 20, respectively, in accordance with the focus movement amount calculated in S705.

As described above, the focusing operations of S702, S703, S705, and S706 executed by the focus detection unit 402 are started by S701, which is executed by the focusing operation starting unit 401, and ended by S704, which is executed by the focusing operation ending unit 403.

Figure 8:
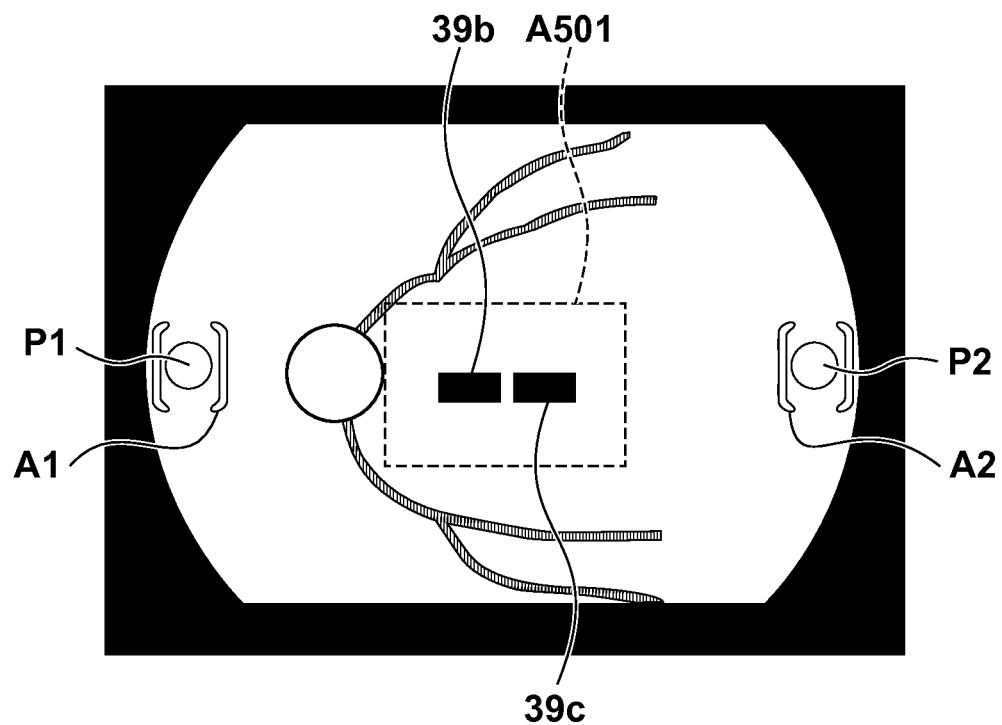
FIG. 8 is a diagram illustrating a fundus image projected in the monitor 15 according to the first embodiment when focusing and alignment are complete.

When the focusing operations described thus far are executed and the focusing operations end, an observation image, such as that shown in FIG. 8, is projected in the monitor 15. By capturing an image in this state, it is possible to obtain an in-focus still image suitable for interpretation.

Next, operations performed by the fundus segment alignment detection unit 32 for implementing the automatic image capturing function according to the present embodiment will be described with reference to FIG. 16 and the flowchart in FIG. 17.

1601 in FIG. 16 indicates a fundus observation image captured by the image sensor 14, and P1 and P2 correspond to the alignment indexes P1 and P2 used to position the ophthalmic imaging apparatus and the eye to be examined as described with reference to FIGS. 1A and 1B. B1 and B2, meanwhile, indicate alignment index detection regions, which will be described later.

Next, operations performed by the fundus segment alignment detection unit 32 will be described with reference to the flowchart in FIG. 17. When fundus segment alignment detection is started, first, in S1701, the fundus segment alignment detection unit 32 requests the image sensor 14 to capture an image. At this time, the light source for capturing the image is set to an infrared wavelength, thus preventing the pupil of the eye to be examined E from constricting.

Next, in S1702, the fundus segment alignment detection unit 32 cuts out images in the alignment index detection regions B1 and B2 from the image captured in S1701.

In S1703, the fundus segment alignment detection unit 32 binarizes the alignment index detection region images cut out in S1702 based on a threshold specified in advance. Examples of images obtained by binarizing the alignment index detection region images are indicated by 1602 and 1603 in FIG. 16.

In S1704, the fundus segment alignment detection unit 32 detects surface areas of images of the alignment indexes P1 and P2 in the alignment index detection region images. In S1705, it is determined whether or not the surface areas of the images of the alignment indexes exceed a specified value. The specified value is defined as, for example, a percentage of the total surface area of the alignment index detection regions taken up by the surface area of the corresponding images of the alignment indexes, and 25% is employed as the value here.

The process advances to S1706 in the case where it has been determined in S1705 that the surface area of the images of the alignment indexes exceeds the specified value. In S1706, the fundus segment alignment detection unit 32 notifies the system control unit 18 that the fundus segment alignment is complete. Meanwhile, the process advances to S1707 in the case where it has been determined in S1705 that the surface area of the images of the alignment indexes is less than or equal to the specified value. In S1707, the fundus segment alignment detection unit 32 notifies the system control unit 18 that the fundus segment alignment is incomplete.

Figure 16:
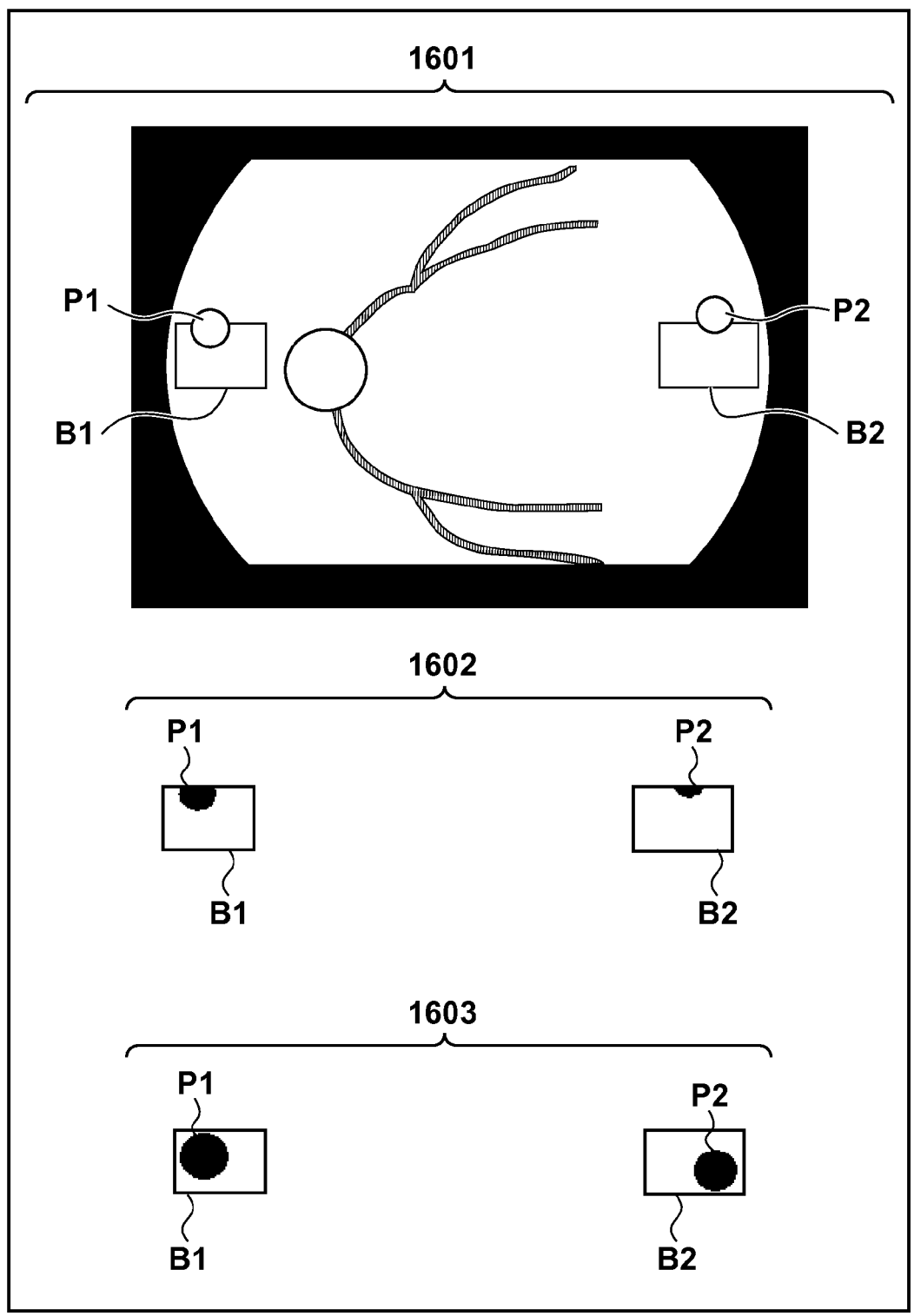
FIG. 16 is a diagram illustrating an example of a fundus image captured by the image sensor 14 according to the first embodiment.
Figure 17:
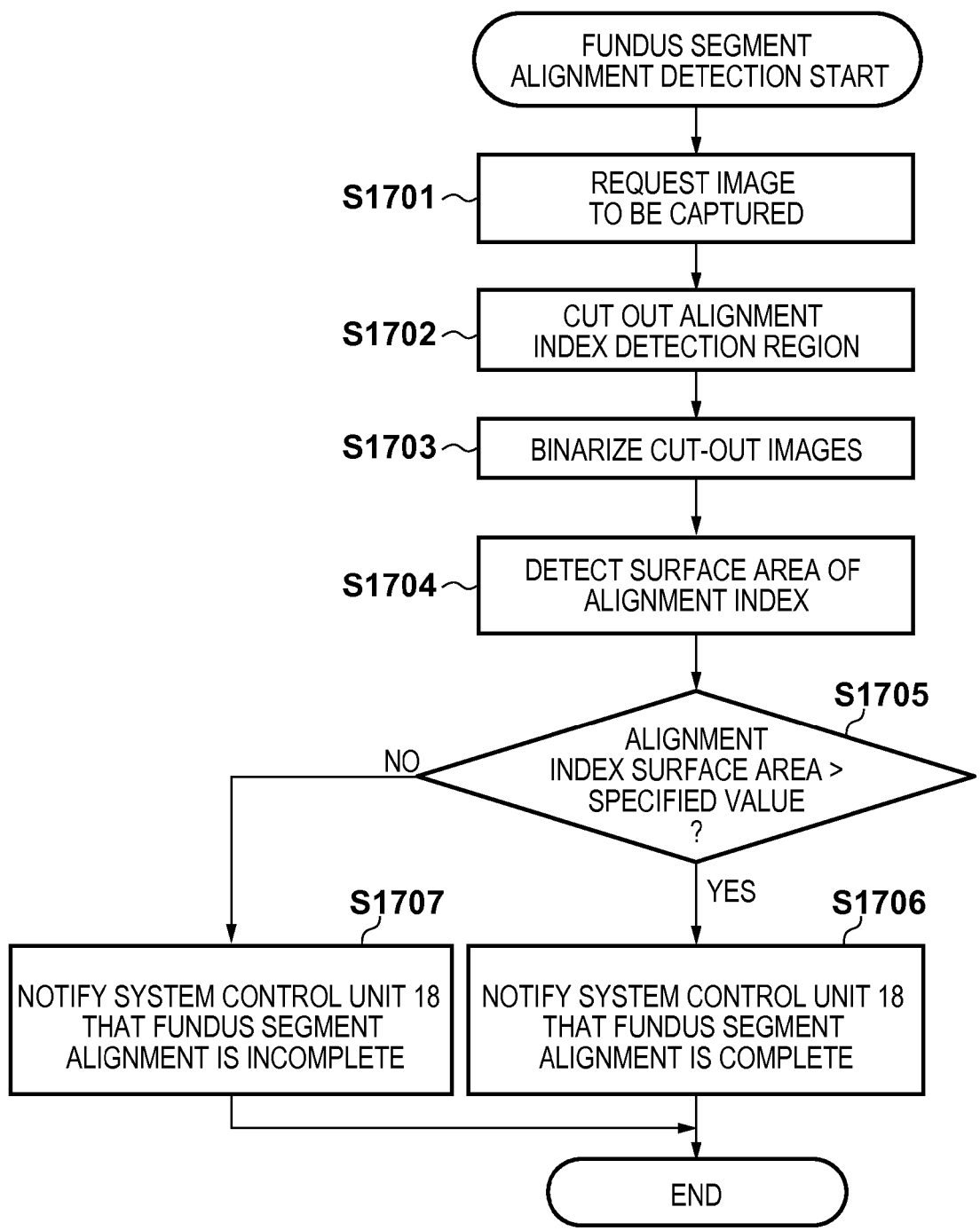
FIG. 17 is a flowchart illustrating operations performed by a fundus segment alignment detection unit according to the first embodiment.

Here, 1602 in FIG. 16 indicates an example of images based on which the system control unit 18 is notified that the fundus segment alignment is incomplete, whereas 1603 indicates an example of images based on which the system control unit 18 is notified that the fundus segment alignment is complete.

Next, characteristic control executed by the ophthalmic imaging apparatus according to the present embodiment will be described with reference to the flowcharts in FIGS. 3A and 3B.

When imaging operations are commenced, in S301, the examiner performs anterior ocular alignment operations by manipulating the joystick 204 so as to move the movable stage 202.

Next, in S302, the anterior ocular segment alignment detection process is carried out. Details of the anterior ocular segment alignment detection process are as described above with reference to FIGS. 9, 10, and 11. Then, in S303, the system control unit 18 determines whether or not a notification that the anterior ocular segment alignment is complete has been received as a result of the anterior ocular segment alignment detection process. In the case where the notification that the anterior ocular segment alignment is complete has not been received in S303, the processes of S301 to S303 are repeated.

However, in the case where the notification that the anterior ocular segment alignment is complete has been received in S303, the system control unit 18 retracts the anterior ocular observation unit 107 from the optical axis L3 in S304 and extinguishes the anterior ocular observation light source 105 in S305.

Next, the focus index illumination LED 25 is lighted in S306. Focusing operations are then carried out in S307. Details of the focusing operations are as described above with reference to FIGS. 4, 5, 6, and 7.

Next, the system control unit 18 lights the LEDs 103a and 103b used for alignment index illumination in S308, and lights the fundus observation light source 1 in S309. Then, in S310, the system control unit 18 determines whether or not the focus manipulation unit 205 has been manipulated by the examiner. In the case where the focus manipulation unit 205 has been manipulated by the examiner, it is determined that the apparatus has transited to a manual mode, and the process advances to S320. In other words, functioning as a first control unit, the system control unit 18 performs control for temporarily deactivating an automatic transition function for transiting from an anterior ocular observation state to a fundus observation state, the autofocus function performed during fundus observation, and the automatic image capturing function performed when fundus alignment is complete, and transits to the manual mode, in response to a user manipulating the focus manipulation unit 205 (a first user operation).

On the other hand, in the case where the focus manipulation unit 205 has not been manipulated by the examiner, it is determined that the mode is an automatic mode, and the process advances to S311. In S311, the examiner carries out fundus alignment operations by manipulating the joystick 204 and moving the movable stage 202.

Next, in S312, the fundus segment alignment detection process is carried out. The fundus segment alignment operations are as described above with reference to FIGS. 16 and 17. Then, in S313, the system control unit 18 determines whether or not a notification that the fundus segment alignment is complete has been received as a result of the fundus segment alignment detection process. In the case where the notification that the fundus segment alignment is complete has not been received in S313, the process returns to S310.

However, in the case where the notification that the fundus segment alignment is complete has been received in S313, focusing operations are carried out in S314.

Next, in S315, the system control unit 18 carries out image capturing operations. After this, the system control unit 18 may perform control for temporarily deactivating the automatic transition function for transiting from the anterior ocular observation state to the fundus observation state, the autofocus function performed during fundus observation, and the automatic image capturing function performed when fundus alignment is complete. In S316, the system control unit 18 may determine whether or not the image capturing operations have ended. The image capturing operations are ended by, for example, user operations for turning the power switch of the apparatus off, an operation for stopping the imaging being accepted, or the like. However, in the case where the image capturing operations are to be continued, the process advances to S317.

In S317, the anterior ocular observation unit 107 is inserted into the optical axis L3. Then, in S318, the system control unit 18 determines a state in which the imaging switch 203 is being depressed by the examiner. Specifically, the system control unit 18 determines whether or not the first-stage switch of the imaging switch 203 has been depressed for greater than or equal to an amount of time prescribed in advance.

In the case where it has been determined that the first-stage switch of the imaging switch 203 has been depressed for greater than or equal to the prescribed time, control is carried out for once again activating the automatic transition function for transiting from the anterior ocular observation state to the fundus observation state, the autofocus function performed during fundus observation, and the automatic image capturing function performed when fundus alignment is complete, if those functions are currently deactivated; the process then returns to S301. On the other hand, in the case where it has been determined that the first-stage switch of the imaging switch 203 has not been depressed for greater than or equal to the prescribed time, the process advances to S319.

In S319, the system control unit 18 determines whether or not the target eye to be imaged has been changed. The determination as to whether or not the target eye to be imaged has been changed is, for example, finding an amount the user has moved the optical main body 200 between a current position of the optical main body 200 on the fixed base 201, illustrated in FIG. 1A, and a position of the optical main body 200 when imaging was carried out in S315, and determining that the target eye to be imaged has been changed in the case where the movement amount exceeds a predefined amount.

In the case where it has been determined in S319 that the target eye to be imaged has been changed, control is carried out for once again activating the automatic transition function for transiting from the anterior ocular observation state to the fundus observation state, the autofocus function performed during fundus observation, and the automatic image capturing function performed when fundus alignment is complete, if those functions are currently deactivated; the process then returns to S301. On the other hand, in the case where it has been determined in S319 that the target eye to be imaged has not been changed, the process returns to S318.

Next, a case where the process has advanced to S320 and the steps subsequent thereto after the determination in S310 will be described. In S320, the system control unit 18 drives the focusing lens 12 in response to the user manipulating the focus manipulation unit 205.

Then, in S321, the system control unit 18 determines a state in which the imaging switch 203 is being depressed by the examiner. In the case where it has been determined in S321 that the first-stage switch of the imaging switch 203 has been depressed for greater than or equal to an amount of time prescribed in advance (that is, that a second user operation has been carried out), the system control unit 18 functions as a second control unit and controls the temporarily-deactivated automatic transition function, autofocus function, and automatic image capturing function to be reactivated; the process then moves to S311. On the other hand, in the case where it has been determined in S321 that the first-stage switch of the imaging switch 203 has not been depressed for greater than or equal to the amount of time prescribed in advance, the process advances to S322. In S322, the system control unit 18 determines whether or not a second-stage switch of the imaging switch 203 is being depressed. In the case where it has been determined in S322 that the second-stage switch of the imaging switch 203 is being depressed, the process moves to S315 and the image capturing process is carried out. On the other hand, in the case where it has been determined in S322 that the second-stage switch of the imaging switch 203 is not being depressed, the process returns to S321.

Figure 3B:
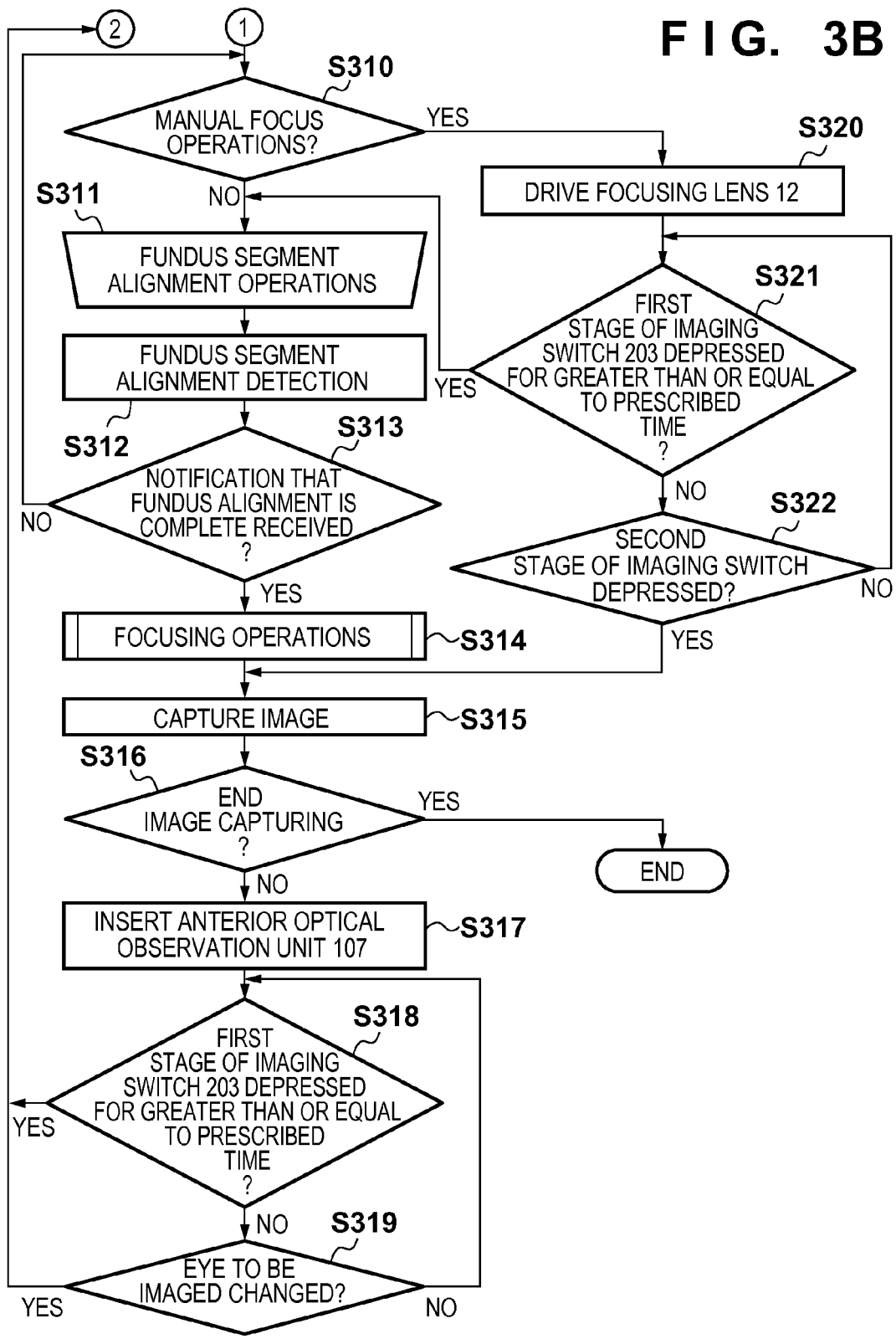

Note that the timing of the processes is not limited to that shown in the flowcharts of FIGS. 3A and 3B, and the configuration may be such that automatic transition function, the autofocus function, and the automatic image capturing function are switched between inactive and active at any timing at which user operations of the focus manipulation unit, the imaging switch, other switches, and so on have been accepted.

As described above, the ophthalmic imaging apparatus according to the present embodiment is configured to temporarily deactivate the automatic transition function for transiting from the anterior ocular observation state to the fundus observation state, the autofocus function performed during fundus observation, and the automatic image capturing function performed when fundus alignment is complete. Accordingly, in the case where it has been determined that further adjustment on the part of the examiner is necessary as a result of the apparatus automatically transiting from the anterior ocular observation state to the fundus observation state or as a result of performing autofocus, the examiner can perform the necessary operations. This improves the usability for the examiner of the ophthalmic imaging apparatus.

Furthermore, the ophthalmic imaging apparatus according to the present embodiment is configured to reactivate the temporarily-deactivated automatic transition function for transiting from the anterior ocular observation state to the fundus observation state, the autofocus function performed during fundus observation, and the automatic image capturing function performed when fundus alignment is complete. Accordingly, the examiner can manually change a focus region and then execute the autofocus function in a region where focusing is possible. This improves the usability for the examiner of the ophthalmic imaging apparatus.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-247754 filed on Nov. 9, 2012, which is hereby incorporated by reference herein in its entirety.

What is claimed is:

1. An ophthalmic imaging apparatus having an automatic transition function for transiting from an anterior ocular observation state to a fundus observation state, an autofocus function performed during fundus observation, and an automatic image capturing function performed when fundus alignment is complete, the apparatus comprising:
   a first control unit configured to control the automatic transition function, the autofocus function, and the automatic image capturing function to be deactivated in response to a first user operation; and
   a second control unit configured to control the deactivated automatic transition function, autofocus function, and automatic image capturing function to be reactivated in response to a second user operation.

2. The ophthalmic imaging apparatus according to claim 1, further comprising:
   a focus operation unit for driving a focus lens,
   wherein the first user operation is a manipulation of the focus operation unit.

3. The ophthalmic imaging apparatus according to claim 1, further comprising:
   an imaging switch capable of being pressed in two stages,
   wherein the second user operation is an operation of pressing a first stage of the imaging switch for greater than or equal to a prescribed time.

4. The ophthalmic imaging apparatus according to claim 3, wherein imaging is executed in response to an operation of pressing a second stage of the imaging switch.

5. The ophthalmic imaging apparatus according to claim 1, wherein the second user operation is an operation that changes a target eye to be imaged; and
   the second control unit is configured to control the deactivated automatic transition function, autofocus function, and automatic image capturing function to be reactivated in the case where the target eye has been changed.

6. A control method for an ophthalmic imaging apparatus having an automatic transition function for transiting from an anterior ocular observation state to a fundus observation state, an autofocus function performed during fundus observation, and an automatic image capturing function performed when fundus alignment is complete, the method comprising:
   a first control step of controlling the automatic transition function, the autofocus function, and the automatic image capturing function to be deactivated in response to a first user operation; and
   a second control step of controlling the deactivated automatic transition function, autofocus function, and automatic image capturing function to be reactivated in response to a second user operation.

7. A non-transitory computer-readable storage medium storing a computer program that causes a computer to execute each process of the control method for an ophthalmic imaging apparatus according to claim 6.

* * * * *